US00PP12383P2

(12) United States Plant Patent
Dransfield

(10) Patent No.: US PP12,383 P2
(45) Date of Patent: Feb. 5, 2002

(54) BUDDLEJA PLANT NAMED 'SANTANA'

(75) Inventor: Rod Dransfield, Knaresborough (GB)

(73) Assignee: Plant haven, Santa Barbara, CA (US)

( * ) Notice: Subject to any disclaimer, the term of this patent is extended or adjusted under 35 U.S.C. 154(b) by 0 days.

(21) Appl. No.: 09/357,526

(22) Filed: Jul. 19, 1999

(51) Int. Cl.[7] ..... A01H 5/00
(52) U.S. Cl. ..... Plt./242
(58) Field of Search ..... Plt./242

(56) References Cited

PUBLICATIONS

GTITM UPOVROM Citation for 'Santana' as per GB PBR 02300204; Jan. 8, 1998.*

* cited by examiner

*Primary Examiner*—Bruce R. Campell
*Assistant Examiner*—Kent L. Bell

(57) ABSTRACT

A new cultivar of *Buddleja davidii* named 'Santana', that is characterized in having yellow to golden leaf margins and purple-red flowers.

2 Drawing Sheets

BACKGROUND OF THE INVENTION

The present invention relates to a new and distinct cultivar of *Buddleja davidii* and will be referred to hereafter as 'Santana'. 'Santana' represents a new Butterfly Bush, a deciduous shrub grown for landscape use.

The new cultivar, 'Santana', was discovered as a sport that appeared on a plant of Buddleja 'Royal Red' (unpatented) in the garden of the inventor in North Yorkshire, UK in 1990. 'Santana' was discovered as a naturally occurring lateral branch mutation of Buddleja 'Royal Red' (unpatented). It was isolated from the parent plant and found to have stable, variegated foliage. The new cultivar can be readily distinguished from other cultivars of *Buddleja davidii* known to the inventor in that the leaf margins are a bright yellow to golden color. The two closest cultivars are 'Harlequin' (unpatented) and 'Masquerade' (unpatented); both have creamy-white leaf margins and purple-red flowers. Leaf margins of 'Santana' are wider than leaf margins of 'Harlequin' and 'Masquerade'. The flower color of 'Santana' is purple-red and essentially the same as 'Royal Red', 'Masquerade' and 'Harlequin'.

Asexual reproduction of the new cultivar was first accomplished by softwood cuttings in Knaresborough, North Yorkshire, UK on July 1990. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar from other commercial varieties known to the inventor.

1. The foliage of 'Santana' has bright yellow to golden margins. The centers are dark green with some mottling of a lighter green. The golden margins are wider than comparative cultivars (3–5 mm). The leaf margins are 1–1.5 mm on 'Harlequin' and 2–3 mm on 'Masquerade'.

2. 'Santana' has sweetly scented purple-red flowers.

3. 'Santana' is a medium-sized cultivar of *Buddleja davidii*, reaching 1.85 M in height with a spread of 1.5 M. Many cultivars can reach 3 M in height and 5 M in width.

4. 'Santana' can be distinguished from 'Royal Red' by its variegation with leaf margins that are 3 to 5 mm in width of a bright yellow to golden color. 'Royal Red' in contrast has leaves that are solid green with no variegation. The flower color and other general characteristics of 'Santana' are similar to those of 'Royal Red'.

BRIEF DESCRIPTION OF THE DRAWING

The photograph on sheet one depicts typical flowers and foliage of 'Santana'.

The photograph on sheet two depicts foliage variegation colors of 'Harlequin', 'Masquerade' and 'Santana' (right to left). The colors are as close as possible with conventional photography.

BOTANICAL DESCRIPTION OF THE PLANT

The following is a detailed description of the new cultivar as grown in a 2 gallon container in North Yorkshire, England. The cultivar shown is a two year old plant.: Phenotypic differences may be observed with variations in environmental, climatic, and cultural conditions. The color determination is in accordance with The R.H.S. Colour Chart of The Royal Horticultural Society, London, England, except where general color terms of ordinary dictionary significance are used.

Botanical classification: 'Santana' is a cultivar of *Buddleja davidii.*

Commercial classification: Butterfly Bush.

Parentage: A naturally occurring lateral branch mutation of Buddleja 'Royal Red' (unpatented).

Plant description:

*Blooming period.*—July to August.

*Blooming habit.*—Rounded-arching with long, slender branches.

*Height and spread.*—1.85 M in height, 1.5 M in width.

*Hardiness.*—Zone 5–9.

*Type.*—Deciduous shrub.

*Root description.*—Fibrous.

*Crop time.*—Semi-hard cuttings develop roots in a 2" liner in 5 weeks at 70 degrees F. From the 2" liners about 12 months are required to produce a fully grown finished flowering plant in a one gallon container.

*Culture.*—Well-drained, moist, loamy soils.

*Diseases and pest.*—Not observed.

Stems:

*Shape.*—Quadrangular.

*Color.*—144C with purple overlay (187A).

*Size.*—Up to 5 mm in diameter.

*Typical stem length of a mature plant.*—1.50 m with occasional stem lengths attaining 1.85 m.

*Internode.*—4–8 cm in length.

*Surface.*—Glaucous.

Leaves:

*Shape.*—Lance-shaped (elliptic proportions).

*Division.*—Simple.

*Base.*—Attenuate.

*Apex.*—Acute.

*Venation.*—Reticulate (not prominent).

*Margins.*—Serrulate.

*Attachment.*—Some leaves are sessile while others are petiolate.

*Petiole.*—3–5 mm in length, 2 mm in diameter, color 144C.

*Arrangement.*—Opposite, secondary leaves/branching.

*Surface.*—Upper; primarily glabrous (more pubescence to young leaves). Lower; pubescent.

*Color.*—Upper; yellow-gold margins 12A with centers 137C blended with some mottling 144B. Centers comprise 40–60% of leaf. Margins are typically 3–5 mm. Early growth is bright and distinct. Lower; 194B.

Flowers:

*Size.*—12 mm in length, 9 mm in diameter at apex, 1 mm in diameter at base.

*Type.*—Dense conical panicle, terminal and axillary.

*Number.*—Approximately 500 per panicle. Panicle color is observed to be identical to flower petal color, that is intermediate color between 74A and 80A.

*Lastingness of the inflorescence.*—3–4 weeks.

*Petal size.*— 4 mm in length, 3 mm in width.

*Petal number.*—4, partly fused.

*Petal apex.*—Rounded.

*Petal margin.*—Serrate.

*Petal texture.*—Glabrous.

*Petal color (both surfaces).*—Intermediate color between 74A–80A (both surfaces), throat 167C.

*Calyx.*—Bell-shaped, color 194A (both surfaces).

*Corolla.*—Tubular.

*Bud shape.*—Linear changing to drumstick. Size 10 mm in length, 1 mm in diameter at base, 1.5 mm in diameter at apex.

*Bud color.*—77A.

Reproductive organs:

*Stamens.*—Stamen number: 4, fused with petals in the flower tube.

*Filament color.*—76B.

*Filament size.*—About 5 mm in length, 0.5 mm in width.

*Anther size.*—About 3 mm in length, 1.5 mm in width.

*Anther shape.*—Oblong.

*Pollen amount.*—Moderate.

*Pollen color.*—195C.

*Pistils.*—Pistil number: 1.

*Pistil size.*—About 4 mm in length, 0.5 mm in width.

*Stigma color.*—195C.

*Ovary position.*—Superior. Ovary color: 195B.

Fragrance: Faint to moderately strong; sweet.

Bracts: Number 2 (one pair).

*Size.*—About 3 cm in length, 0.7 cm in width.

*Texture.*—Glabrous.

*Color.*—137C (upper surface), 194B (lower surface).

Stipules:

*Shape.*—Reniform.

*Size.*—About 5 mm in length, about 8 mm in width.

*Margins.*—Smooth.

*Texture.*—Coriaceous.

*Color.*—137B (both surfaces).

Fruit: Elongated capsule, 8.5 mm in length, 2.5 mm in diameter, color 145A with an overlay of 77A, approximately 50 capsules per panicle.

*Seeds.*—Approximately 30 per capsule, approximately 0.75 mm in length and 0.5 mm in width, color 165C.

TABLE 1

| | 'Harlequin' | 'Masquerade' | 'Santana' |
|---|---|---|---|
| Leaf Colors upper surface: | | | |
| Center | 137C | 137C | 137C |
| Center Mottling | 138C | 138C | 144B |
| Margin | mixture of 11B-11C | mixture 11B-11C | 12A |
| Leaf Colors lower surface: | 194B | 194C | 194B |
| Margins upper surface: | | | |
| Width | 1–1.5 mm | 2–3 mm | 3–5 mm |
| % Coverage | 5–10% | 10–20% | 40–60% |

Flower Color both surfaces:
'Harlequin' intermediate between the two color designations 74A-80A
'Masquerade' intermediate between the two color designations 74A-80A
'Santana' intermediate between the two color designations 74A-80A

I claim:

1. A new and distinct *Buddleja davidii* plant named 'Santana', as illustrated and described.

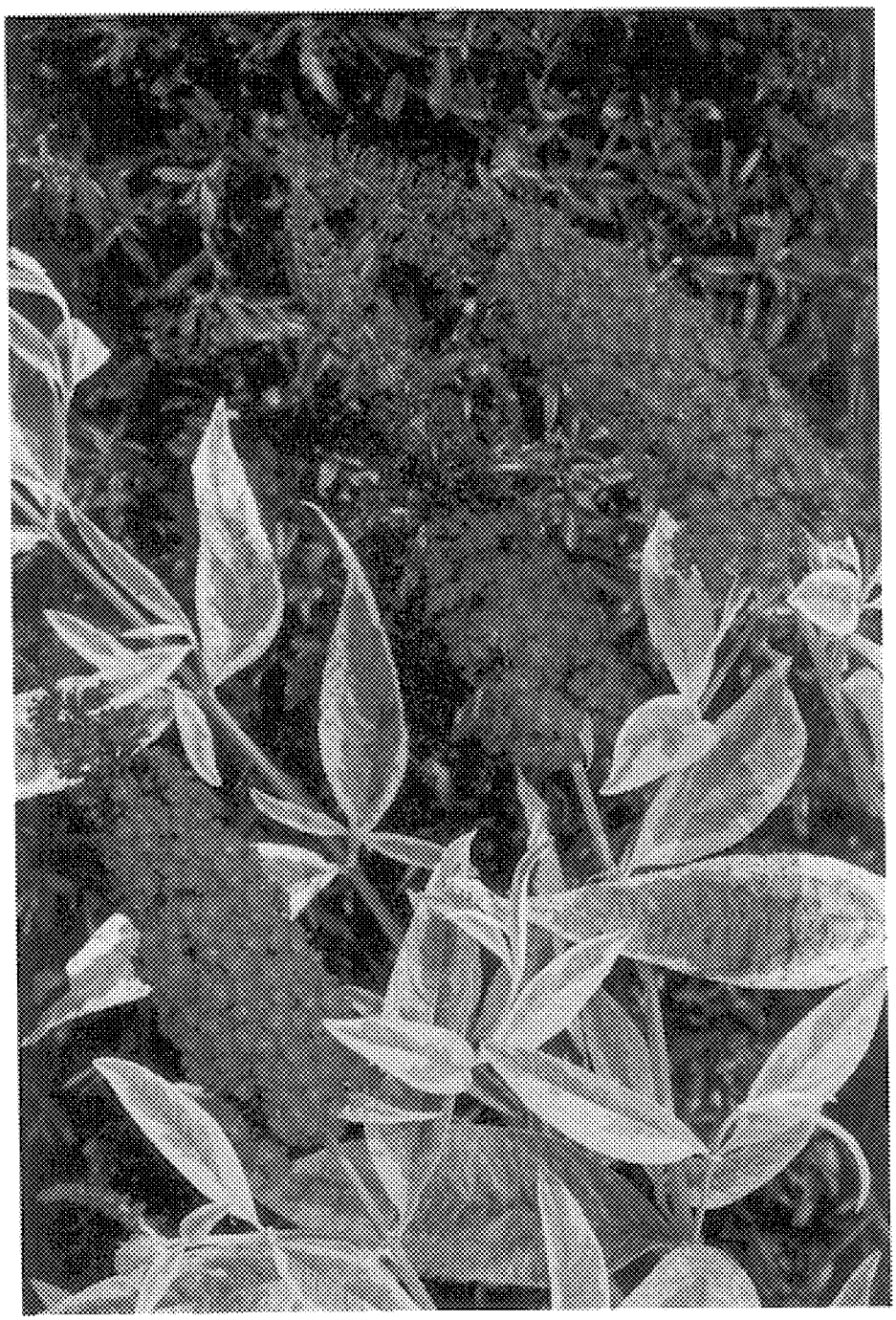

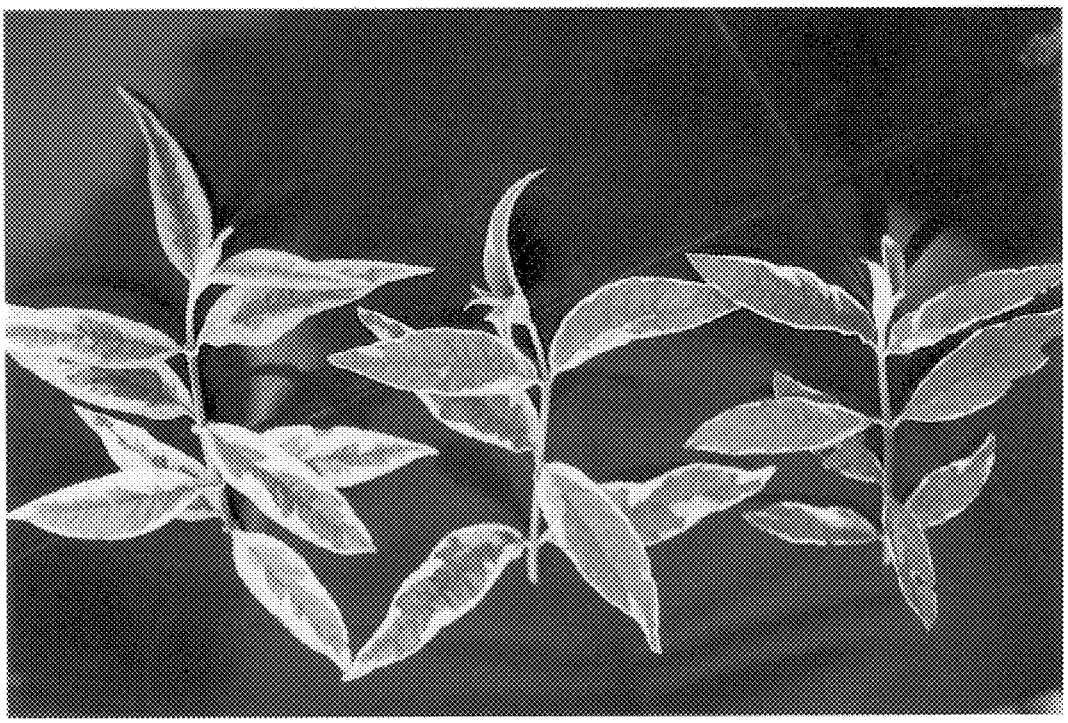

* * * * *